United States Patent
Singh et al.

(12)

(10) Patent No.: US 6,211,428 B1
(45) Date of Patent: *Apr. 3, 2001

(54) TRANSGENIC MOUSE EXPRESSING A FAMILIAL FORM OF HUMAN AMYLOID PRECURSOR PROTEIN

(75) Inventors: Gurparlash Singh, Bedminster; Howard Y. Chen, Westfield, both of NJ (US); Robert P. Heavens, Harlow (GB); Dalip J. S. Sirinathsinghji, Harlow (GB); David W. Smith, Harlow (GB); Myrna E. Trumbauer, Yardley, PA (US); Leonardus H. T. Van Der Ploeg, Scotch Plains, NJ (US); Aurawan Vongs, Sewell, NJ (US); Hui Zheng, Edison, NJ (US)

(73) Assignee: Merck & Co., Inc., Rahway, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/793,558

(22) PCT Filed: Aug. 28, 1995

(86) PCT No.: PCT/US95/10920

§ 371 Date: Apr. 28, 1997

§ 102(e) Date: Apr. 28, 1997

(87) PCT Pub. No.: WO96/06927

PCT Pub. Date: Mar. 7, 1996

Related U.S. Application Data

(63) Continuation of application No. 08/299,872, filed on Sep. 1, 1994, now abandoned.

(51) Int. Cl.[7] .................. A01K 67/00; A01K 67/027; A01K 67/033; G01N 33/00
(52) U.S. Cl. ........................... 800/13; 800/3; 800/18
(58) Field of Search .................. 800/2, 3, 13, 18; 435/172.3, 29, 354; 514/1

(56) References Cited

U.S. PATENT DOCUMENTS 5,087,571 * 2/1992 Leder et al. ............... 435/240.2
5,387,742 * 2/1995 Cordell et al. ............... 800/2

FOREIGN PATENT DOCUMENTS 0 451 700 A1 * 4/1991 (EP) .
WO 9119810 * 12/1991 (WO) .
WO 9206187-A * 4/1992 (WO) .
WO 9213069-A * 8/1992 (WO) .
WO 9302189-A * 2/1993 (WO) .
WO 9314200-A * 7/1993 (WO) .

OTHER PUBLICATIONS

Lannfelt et al (1993) Behav. Brain Res. 57,207 213.*
Chartier–Harlin, et al., :Early–onset Alzheimer's disease caused by mutations at codon 717 of the beta–amyloid precursor protein gene, Nature, vol. 353, pp. 844–846 (1991).*
Chen, et al., "A Lymphoproliferative Abnormality Associated with Inappropriate Expression of the Thy–1 Antigen in Transgenic Mice", Cell, vol. 51, pp. 7–19 (1987).*
Carporaso, et al., "Chloroquine Inhibits intracellular degradation but not secretion of Alzheimer Beta/A4 amyloid precursor protein", PNAS, vol. 89, pp. 2252–2256 (1992).*
Quon, et al., "Formation of Beta–amyloid protein deposits in brains of genic mice", Nature, vol. 352, pp. 239–241 (1991).*
Selkoe, et al., "In the beginning . . . ", Nature, vol. 354, pp. 452–433 (1991).*
De Feudis, et al., "Beta–Amyloid protein in Transgenic Mice", Drug News and Perspectives, vol. 4, pp. 614–619 (1991).*

* cited by examiner

Primary Examiner—Deborah Crouch
(74) Attorney, Agent, or Firm—Michael D. Yablonsky; Jack L. Tribble

(57) ABSTRACT

Transgenic non-human mammals which express in their brains a nucleic acid construct comprising a DNA sequence encoding a human amyloid precursor protein FAD variant where at amino acid position 717 valine is substituted by isoleucine. These transgenic non-human mammals can be assays systems for determining compounds which are effective in modulating production of human amyloid precursor protein in brain and in isolated neuronal cells. Specifically exemplified are transgenic mice whose genome comprises a DNA sequence encoding a human amyloid precursor protein FAD variant where at amino acid position 717 valine is substituted by isoleucine operably linked to a Thy-1 promoter. The mice are shown to produce the APP-FAD variant in their brains by mRNA and protein assays.

6 Claims, 7 Drawing Sheets

```
         10             20             30             40
          *              *              *              *
ACA AAT ATC AAG ACG GAG GAG ATC TCT GAA GTG AAG ATG GAT GCA GAA
 T   N   I   K   T   E   E   I   S   E   V   K   M   D   A   E 50             60             70             80             90
  *              *              *              *              *
TTC CGA CAT GAC TCA GGA TAT GAA GTT CAT CAT CAA AAA TTG GTG TTC
 F   R   H   D   S   G   Y   E   V   H   H   Q   K   L   V   F 100            110            120            130            140
  *              *              *              *              *
TTT GCA GAA GAT GTG GGT TCA AAC AAA GGT GCA ATC ATT GGA CTC ATG
 F   A   E   D   V   G   S   N   K   G   A   I   I   G   L   M 150            160            170            180            190
  *              *              *              *              *
GTG GGC GGT GTT GTC ATA GCG ACA GTG ATC |ATC| ATC ACC TTG GTG ATG
 V   G   G   V   V   I   A   T   V   I  | I |  I   T   L   V   M 200            210            220            230            240
  *              *              *              *              *
CTG AAG AAG AAA CAG TAC ACA TCC ATT CAT CAT GGT GTG GTG GAG GTT
 L   K   K   K   Q   Y   T   S   I   H   H   G   V   V   E   V 250            260            270            280
  *              *              *              *
GAC GCC GCT GTC ACC CCA GAG GAG CGC CAC CTG TCC AAG ATG CAG CAG
 D   A   A   V   T   P   E   E   R   H   L   S   K   M   Q   Q 290            300            310            320            330
  *              *              *              *              *
AAC GGC TAC GAA AAT CCA ACC TAC AAG TTC TTT GAG CAG ATG CAG AAC
 N   G   Y   E   N   P   T   Y   K   F   F   E   Q   M   Q   N

339

TAG
 *
```

FIG.7

TRANSGENIC MOUSE EXPRESSING A FAMILIAL FORM OF HUMAN AMYLOID PRECURSOR PROTEIN

CROSS-RELATED TO OTHER APPLICATIONS

This is a National Stage filing of PCT/US95/10920 under 35 U.S. C. §371 and a continuation of 08/299,872, filed Sep. 1, 1994, now abandoned.

FIELD OF THE INVENTION

The present invention relates to the brain-specific expression of the Familial Alzheimer's disease (V-I) variant of the human amyloid precursor protein in transgenic mice.

BRIEF DESCRIPTION OF THE DRAWINGS

FIG. 7. The 43 amino acid β-A4 domain of FAD APP 751 is shown in bold. The V-I substitution is boxed. The nucleotide sequence in this figure is SEQ ID NO:6 and the amino acid sequence is SEQ ID NO:7.

BACKGROUND OF THE INVENTION

Figure 1:
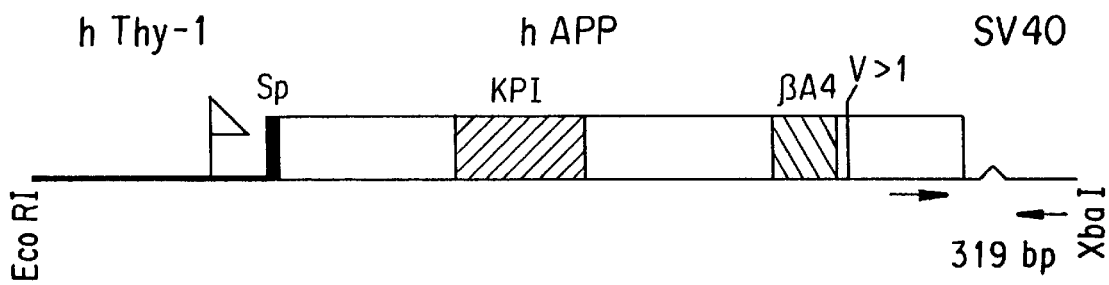
FIG. 1. Schematic representation of the 7.1 kb Eco RI-Xba I fragment encoding the human Thy-1 promoter, the human APP 751 FAD (V-I) cDNA and SV40 derived 3' flanking sequences. Relevant regions of the APP including the signal peptide (Sp), Kunitz protease inhibitor (KPI) and βA4 domains and the position of the V-I FAD mutation are indicated. The position of primers is shown by arrows. The primers were employed across the 66 bp SV40 small t intron (indentation in the physical map) to amplify a 319 bp fragment from the APP 751 FAD mRNA by RT-PCR.

Alzheimer's disease (AD) is a neurological disorder that disproportionately affects the population over 65 years of age. Incidence of the disease increases from less than 1% at age 60–65, to 5% at age 75, to as high as 47% at age 85. Between, 60% to 80% of all cases of dementia in persons over age 65 are caused by AD. Afflicted individuals exhibit impaired cognitive function and memory. Neither a suitable diagnostic procedure nor an effective therapeutic treatment exists for AD. Positive identification of AD requires biopsy or autopsy of the brain.

Although the etiology of AD is unknown, genetic, immunological and environmental factors have been implicated in the development of AD. Distinguishing features of AD include the presence of senile plaques as well as, neurofibrillary tangles and extensive neuronal loss in the neocortex, hippocampus and associated structures. Senile plaques consist of extracellular deposits containing a β-amyloid core surrounded by a halo of dystrophic neurites, glia and astrocytes. β-amyloid deposits are present in neocortex blood vessel walls. The major component of senile plaques is a 4 kDa peptide referred to as βA4, that is proteolytically cleaved from a larger 120 kDa amyloid precursor protein (APP). Other components of the plaques include ubiquitin, amyloid P, Apo E, interleukin-1, and α-1-antichymotrypsin.

In addition to biochemical evidence supporting βA4 involvement in AD, there are strong genetic data which suggest a link between APP and AD. A clue to the location of a gene involved in AD comes from analysis of Down syndrome patients; in these patients trisomy of chromosome 21 is responsible for the early onset of AD. Karyotype analysis of Down syndrome patients mapped the gene involved to the upper portion of the long arm of chromosome 21. The region involved encodes several genes, including the APP gene. The early onset (~ age 35) of AD in Down syndrome patients suggests that an increase in the gene dosage of the responsible marker(s) on the long arm of chromosome 21 may contribute to the neuropathology noticed in most AD patients.

Although the majority of AD cases appear sporadic, several cases of early onset familial AD (FAD) have been reported. Genetic analysis of FAD families has established that the disorder is inherited as a dominant autosomal gene defect, which maps to the long arm of chromosome 21 and is closely linked to the APP gene. These findings are consistent with genetic data obtained from the analysis of Down syndrome patients. Several FAD families have also been identified in which an early onset of AD is strictly correlated with the presence of a mutation in exon 17 of the APP gene at amino acid 717 (Val-Ile). This mutation within the transmembrane spanning domain of the APP co-segregates with FAD. Since the families afflicted with APP717 FAD are of different ethnic origins (English, Japanese and Canadian), evidence for the involvement of the FAD gene in these cases of AD is strong. The mutation is absent from control individuals, in sporadic AD patients, in Down syndrome patients, in late onset familial AD, and also in most other cases of early onset FAD. Several additional mutations in the APP gene have been identified that can explain the occurrence of AD in other FAD families. The genetic evidence in the five distinct early onset $APP_{717}$ FAD families strongly supports the hypothesis that the $APP_{717}$ gene in these FAD families is directly positioned in the pathway of AD progression.

The APP gene is approximately 400 kb in length and encodes a glycosylated, transmembrane protein which may be involved in cell-cell interaction. The APP gene has at least 19 exons that create at least 5 distinct APP transcripts by alternative splicing. The predominant transcripts encode proteins of 695, 751 and 770 amino acids (these major forms of APP are referred as APP 695, APP 751 and APP 770, respectively). Transcripts for APP 695 are enriched in the brain. Transcripts encoding APP 751 and APP 770 mRNA species predominate in peripheral tissues. All three isoforms contain the 42 amino acid βA4 domain. APP isoforms 751 and 770 contain an additional 56 amino acid insert encoding the kunitz type serine protease inhibitor (KPI). APP is proteolytically metabolized by at least two pathways. One pathway involves an α-secretase cleavage site positioned between Lys 16 and Leu 17 of βA4 domain; proteolytic cleavage at this site precludes the formation of amyloidogenic βA4 entity. The second pathway produces intact, amyloidogenic βA4 (39–42 amino acids) by proteolytic cleavages at the β- and γ-secretase cleavage sites of the full-length APP molecule.

The βA4 laden senile deposits seen in AD patients are also found in aged humans and other aged mammals including non-human primates, polar bears and dogs. However, other aged mammals, such as laboratory rats and mice, do not normally develop βA4 deposits. The lack of a cost-effective, experimental animal model mimicking human pathogenesis hinders the understanding AD neuropathology and developing therapeutics against AD. Transgenic technology may offer a suitable alternative to this problem. Addition of a gene construct directing high levels of human APP or its components to key regions in the murine central nervous system may cause neuropathological changes resembling the AD phenotype. Although it may not be possible to produce all aspects of human AD together in a transgenic rodent model, significant aspects of the disease are likely to be produced in an appropriate transgenic animal model.

Accordingly, it is an object of the present invention to provide a transgenic mouse which exhibits neuropathology due to the overexpression of the human FAD APP 751 (V-I) isoform. The FAD APP 751 (V-I) isoform is specifically overexpressed in the brain of patients with familial AD and, therefore, represents a useful and novel model, distinct from those established by others. The transgenic mice of the present invention are useful in the identification of new targets in AD since the progression of the disease can be followed gradually. The mice of the present invention may be used in the identification of compounds that affect the role of FAD APP 751 (V-I) in neuronal dysfunction and compounds that affect formation of βA4 precipitates and/or βA4 function. It is expected that the amino acid substitution in the FAD APP (V-I) protein alters the normal function of the APP protein, thus precipitating early onset AD. Altered APP processing and/or an altered APP function in the mutant protein may thus be responsible for FAD in these cases.

Attempts to express human amyloid precursor protein segments or the full-length wild type protein in transgenic animals have been successful. Numerous reports exist outlining expression of different wildtype, full-length and truncated APP cDNA isoforms in mouse (Kammesheidt et al., (1992) *Proc. Natl. Acad. Sci.*, 89, 10857–10861; Sandhu et al., (1991) *J. Biol. Chem.*, 266, 21331–21334; Quon, et al., (1991) *Nature*, 352, 239–241; Wirak et al., (1991) *Science*, 253, 323–325; Kawabata et al., (1991) Nature 354, 476–478; Patent, International publication number WO93/02189, Neve, R., Inventor). However, these previous attempts to generate transgenic mouse models for AD have essentially failed. One of the main issues has been that in none of these publications researchers have reproducibly identified: i) a high level expression of full-length recombinant human APP protein expressed from cDNA constructs in mouse brain; ii) APP protein deposits in brain; or iii) neuropathology (Jucker et al., (1992) *Science*, 255, 1443–1445; Wirak et al., (1992) *Science*, 255, 1445; Marx, (1992) *Science* 255, 1200–1202; Kawabata, et al., Nature (1992) 356, p 23).

Overexpression of the APP 751 (V-I) cDNA representing a familial ($APP_{717}$) form of AD using a strong neuronal-specific promoter has not been attempted by others and is a unique aspect of the animal model described herein. The mouse of the present invention differs from others in that it shows a high steady state expression of APP 751 FAD protein by Western blotting, a unique distribution of APP mRNA in the central nervous system by in situ hybridization, and a unique deposition of intraneural protein APP FAD aggregates. These characteristics of the invention in combination with the identification of neuronal βA4 immunoreactive aggregates extend beyond previous claims in this area of research. Because of the early onset of FAD, this disease differs from late life AD. The model presented here will therefore represent unique aspects of AD.

SUMMARY OF THE INVENTION

A transgenic mouse with brain-specific expression of the familial form of the APP 751 isoform with a valine to isoleucine substitution at amino acid 698 (APP 751 isoform numbering; previously introduced as $APP_{717}$ based on APP 770 isoform numbering) is provided. The transgenic mouse of the invention may be used in the study of AD and disorders involving the central nervous system.

DETAILED DESCRIPTION OF THE INVENTION

A transgenic mouse with brain-specific expression of the familial form of the APP 751 isoform with a valine to isoleucine substitution at amino acid 698 (APP 751 isoform numbering; previously introduced as $APP_{717}$ based on APP 770 isoform numbering) is provided. The transgenic mouse of the invention may be used in the study of AD and disorders involving the central nervous system.

The term "animal" is used herein to include all vertebrate animals, except humans. It also includes an individual animal in all stages of development, including embryonic and fetal stages. A "transgenic animal" is an animal containing one or more cells bearing genetic information received, directly or indirectly, by deliberate genetic manipulation at a subcellular level, such as by microinjection or infection with recombinant virus. This introduced DNA molecule may be integrated within a chromosome, or it may be extra-chromosomally replicating DNA. The term "germ cell-line transgenic animal" refers to a transgenic animal in which the genetic information was introduced into a germ line cell, thereby conferring the ability to transfer the information to offspring. If such offspring in fact possess some or all of that information, then they, too, are transgenic animals.

The information may be foreign to the species of animal to which the recipient belongs, foreign only to the particular individual recipient, or genetic information already possessed by the recipient. In the last case, the introduced gene may be differently expressed compared to the native endogenous gene.

The genes may be obtained by isolating them from genomic sources by preparation of cDNAs from isolated mRNA templates, by directed synthesis, or by some combination thereof.

To be expressed, the structural gene must be coupled to a promoter in a functional manner. Promoter/regulatory sequences may be used to increase, decrease, regulate or designate to certain tissues or to certain stages of development the expression of a gene. The promoter need not be a naturally occurring promoter. In the preferred embodiment of the invention, the human Thy-1 (hThy-1) promoter is used. The hThy-1 promoter preferentially allows expression of the gene of interest within the brain (Gordon, J. et al., (1987) *Cell*, 50, 445–452).

The "transgenic non-human animals" of the invention are produced by introducing "transgenes" into the germline of the non-human animal. The methods enabling the introduction of DNA into cells are generally available and well-known in the art; however, the generation of a particular type of transgenic animal requires experimentation. Different methods of introducing transgenes could be used. Generally, the zygote is the best target for microinjection. In the mouse, the male pronucleus reaches the size of approximately 20 μm in diameter, which allows reproducible injection of 1–2 pL of DNA solution. The use of zygotes as a target for gene transfer has a major advantage, in most cases, the injected DNA will be incorporated into the host gene before the first cleavage (Brinster, et al., (1985) *Proc. Natl. Acad. Sci. USA* 82, 4438–4442). Consequently, nearly all cells of the transgenic non-human animal will carry the incorporated transgene. Generally, this will also result in the efficient transmission of the transgene to offspring of the founder since 50% of the germ cells will harbor the transgene. Microinjection of zygotes is the preferred method for incorporating transgenes in practicing the invention.

Retroviral infection can also be used to introduce a transgene into a non-human animal. The developing non-human embryo can be cultured in vitro to the blastocyst stage. During this time, blastomeres may be targets for retroviral infection (Jaenich, R. (1976) *Proc. Natl. Acad. Sci. USA* 73, 1260–1264). Efficient infection of the blastomeres is obtained by enzymatic treatment to remove the zona pellucida (Hogan et al., (1986) in Manipulating the Mouse Embryo, Cold Spring Harbor Laboratory Press, Cold Spring Harbor, N.Y.). The viral vector system used to introduce the transgene is typically a replication-defective retrovirus carrying the transgene (Jahner et al., (1985) *Proc. Natl. Acad. Sci. USA* 82, 6927–6931; Van der Putten et al., (1985) *Proc. Natl. Acad. Sci. USA* 82, 6148–6152). Transfection is easily and efficiently obtained by culturing the blastomeres on a monolayer of virus-producing cells (Van der Putten, supra; Stewart et al., (1987) *EMBO J.* 6: 383–388). Alternatively, infection can be performed at a later stage. Virus or virus-producing cells can be injected into the blastocoele (Jahner et al., (1982) *Nature* 298: 623–628). Most of the founder animals will be mosaic for the transgene since incorporation occurs only in a subset of the cells which formed the transgenic non-human animal. Furthermore, the founder animal may contain retroviral insertions of the transgene at a variety of positions in the genome; these generally segregate in the offspring. In addition, it is also possible to introduce transgenes into the germ line, albeit with low efficiency, by intrauterine retroviral infection of the midgestation embryo (Jahner et al., (1982) supra).

A third type of target cell for transgene introduction is the embryonal stem cell (ES). ES cells are obtained from pre-implantation embryos cultured in vitro (Evans, M. J., et al., (1981) *Nature* 292, 154–156; Bradley, A., et al., (1984) *Nature* 309, 255–258; Gossler, et al., (1986) *Proc. Natl. Acad. Sci. USA* 83, 9065–9069; and Robertson, et al., (1986) *Nature* 322, 445–448). Transgenes can be efficiently introduced into ES cells by DNA transfection or by retrovirus-mediated transduction. The resulting transformed ES cells can thereafter be combined with blastocysts from a non-human animal. The ES cells colonize the embryo and contribute to the germ line of the resulting chimeric animal (For review see Jaenisch, R. (1988) *Science* 240, 1468–1474).

The methods for evaluating the presence of the introduced DNA as well as its expression are readily available and well-known in the art. Such methods include, but are not limited to DNA (Southern) hybridization to detect the exogenous DNA, polymerase chain reaction (PCR), polyacrylamide gel electrophoresis (PAGE) and Western blots to detect DNA, RNA and protein. The methods include immunological and histochemical techniques to detect amyloid precursor protein and pathology associated with Alzheimer's disease.

As used herein, a "transgene" is a DNA sequence introduced into the germline of a non-human animal by way of human intervention such as by way of the methods described below.

A potential therapeutic compound for AD may be detected by measuring its capacity to block the neurodegenerative effect of APP, to block expression of APP, or to evaluate neurotrophic or other neuronally active compounds in these transgenic mice possibly in combination with different genetic backgrounds or transgenes, providing other susceptibility markers (i.e., cytokines, apolipoprotein overexpression and knock out, protease inhibitors, serum amyloid protein, NGF receptor protein, and prion protein transgenic mice). Such compounds will be formulated in accordance with known methods to produce pharmaceutically acceptable compositions. Such compositions may be administered to patients in a variety of standard ways.

The following is presented by the way of examples and is not to be construed as a limitation on the scope of the invention:

EXAMPLE 1
Construction of Human APP 751 FAD Expression Vector Using the Neuronal-specific Human Thy-1 Promoter
A. Construction of pHZ024, a Plasmid Containing Human Thy-1 and SV40 Sequences A 3.7 kb Eco RI-Bgl II fragment of pBSHT1 containing the human Thy-1 promoter and the ATG translation initiation codon of the the Thy-1 gene was cloned into the Eco RI-Bam HI site of pTZ18u to generate pHZ020. We needed to remove the ATG translation initiation codon derived from the Thy-1 gene, allowing the ATG from any new coding sequence that we wished to introduce, downstream of the Thy-1 promoter to encode the first translation initiation start site. Therefore, a 1.6 kb Bam HI-Bgl 11 fragment of pBSHT1 (encoding the ATG translation initiation codon) was subcloned into the Bam HI site of pTZ18u to generate pHZ021a. To silence the initiation codon and to add convenient cloning sites, PCR amplification was carried out using pHZ021a as template and 20-mer (T7; 5' primer) and 73-mer (oHZ002; 3' primer with disrupted ATG and several convenient cloning sites) oligonucleotides. In primer oHZ002 the ATG translation initiation codon has been mutated and replaced with a Hind III restriction enzyme site (see sequence given below; the Hind III restriction enzyme site is outlined in bold; mutated residues are underlined).

```
T7   :   5'TAATACGACTCACTATAGGG (SEQ ID NO: 1).
oHZ002:  5'ACGTCGACTCTAGAAGATCTTCGACTCGAGATCGATGGTACCCGGGCAGGTT-
         CAAGCTTCTGGGATCTCAGTC (SEQ ID NO: 2).
         CATGGTTCTGGGATCTCAGTC (unaltered strand)
```

Incorporation of the underlined residues in the 1.3 kb amplified product destroyed the ATG (CAT in the unaltered complimentary strand, shown in italics) but created a Hind III site (in bold letters). The modified Thy-1 promoter was reconstituted by ligating 0.3 kb Nco I-Xba I fragment of the 1.3 kb amplified product into Nco I-Xba I digested pHZ020. The resulting vector is designated pHZ022.

SV40 sequences were inserted into this plasmid downstream of the Thy-1 promoter in a two step procedure; first, by inserting a Bgl II linker at the Sma I restriction enzyme site upstream of the SV40 small t intron of pSV2neo (pHZ023; Southern and Berg, (1982) Mol, Appl. Genet. 1:327) and second by isolating the 1.0 kb Bgl II-Bam HI containing SV40 small t intron and polyadenylation site and ligating it to the Bgl II digested pHZ022. In the resulting plasmid, pHZ024, the neuronal specific human Thy-1 promoter is separated from the SV40 sequences by a multi-purpose cloning site, permitting the insertion of desired gene(s) or their segments.
B. Construction of APP 751 FAD Expression Vector, p4

A 2.7 kb Sma I-Cla I restriction fragment encoding the full-length human APP 751 cDNA with the late onset FAD mutation (V-I) was obtained by restriction enzyme digestion of plasmid DA-12 (a gift of Drs. N. Robakis of Mount Sinai School of Medicine and R. Swanson of MRL, West Point). The ends of the Sma I-Cla I restriction enzyme fragment were made blunt with the Klenow fragment of DNA polymerase I. This fragment was ligated into pHZ024 (pHZ024 was digested with Xho I and the Xho I site was made blunt using the Klenow fragment of DNA polymerase I). The human APP 751 cDNA (V>I) was thus placed under the control of the hThy-1 promoter, flanked at its 3' end by the SV40 small t intron and poly A addition site. The resulting plasmid is referred to as p4. The nucleotide sequence of the coding sequence of the APP 751 cDNA insert of plasmid p4 was entirely confirmed to assure that the entire amino acid sequence was as predicted and a full-length polypeptide would be expressed. A 79 bp deletion in the 3' non coding extension of the mRNA of APP 751 was noted. For microinjection into zygotes, the p4 expression vector was purified on a CsCl gradient and was digested at a unique Xba I restriction enzyme site and partially restriction enzyme digested with Eco RI to obtain a 7.1 kb fragment, T-APP751 FAD, which does not contain flanking plasmid sequences. The 7.1 kb fragment was purified on a preparative 1% low melting point agarose gel containing 10 ng/ml ethidium bromide. The DNA was visualized using minimal exposure to short-wave UV light and the 7.1 kb band was excised, melted at 65–70° C., phenol/chloroform extracted twice, chloroform extracted once and ethanol precipitated in 0.3 M sodium acetate (pH 5.2) and filtered through a pre-rinsed 0.2 $\mu$m cellulose acetate filter. The purified 7.1 kb linear DNA containing the human Thy-1 promoter linked to the human APP 751 FAD cDNA and SV40 small t intron and poly A addition sequences was subsequently microinjected (FIG. 1).

All restriction endonucleases and DNA modifying enzymes were from Boehringer Mannheim, Inc. DNA sequencing was performed using either Sequenase (U.S. Biochemical, Inc.) or a double stranded DNA Cycle Sequencing Kit (BRL, Inc.). Oligodeoxynucleotides were synthesized on ABI DNA Synthesizer model #381A. PCR was according to Perkin-Elmer, Corp.

EXAMPLE 2
Production of Transgenic Mice Containing Human Amyloid Precursor Protein Under Regulation of the Human Thy-1 Promoter The p4 DNA construct of Example 1 containing the human APP 751 FAD cDNA under the control of the human Thy-1 promoter was microinjected into the pronucleus of one-cell fertilized mouse embryos obtained from superovulated B6SJL females. The optimal concentration of the DNA used for microinjection was the $LD_{50}$ value derived empirically from toxicity test experiments using several dilutions of the gene construct microinjected into mouse embryos. This LD50 value came out to be $7.5 \times 10^{-9}$ $\mu$g. The embryos injected with $7.5 \times 10^{-9}$ $\mu$g DNA were then surgically reimplanted into the oviducts of pseudopregnant recipient mice and allowed to develop to term. At three to four weeks, postnatal tail samples were taken by clipping approximately 1 cm of the tail for DNA (Southern) blot analysis to determine the presence of the transgene. Necropsies and/or biopsies were performed to collect tissue specimens for histological and expression studies.

EXAMPLE 3
Analysis of Transgenic Mice
A. DNA Analysis

Genomic DNA extracted from tail samples using a Proteinase-K lysis method was quantitated by DNA fluorometry. Approximately 7 mg of genomic DNA was digested with the restriction enzyme Bam HI, size separated on a 0.8% agarose gel, after which the DNA was transferred to a nylon membrane by Southern blotting. The filters were hybridized with transgene-specific $^{32}$p labeled SV40 sequences. Hybridization was conducted at 65° C. in 6×SSC, 5× Denhardt's reagent, 50% Dextran sulphate, 1.2% SDS, 100 mg/ml denatured, sonicated salmon sperm DNA, and 0.1 M Tris (pH 7.4). Post-hybridizational washes were performed in 2×SSC, 1% SDS for 15 minutes at room temperature followed by serial washes 65° C. in 2×SSC, 1% SDS for 2–3 hours. The filters were exposed to X-ray film at –70° C. with an intensifying screen for up to five days. Transgene copy number was determined on 7 μg of genomic DNA from transgenic offspring with known quantities of the linearized p4 vector co-migrated in the same agarose gel. The probe used was able to detect as little as 0.1 copies of the transgene in the murine genome. Appropriate transgenic founders were bred to produce offspring. Three transgenic founders were numbered 7.2, 9.3 and 14.2. The transgene copy number in these three founders ranged from 1–5 in the F1 progeny of the 7.2 and 14.2 founders, and 6–10 for the F1 progeny of the 9.3 founder.

B. RNA Analysis

Figure 2:
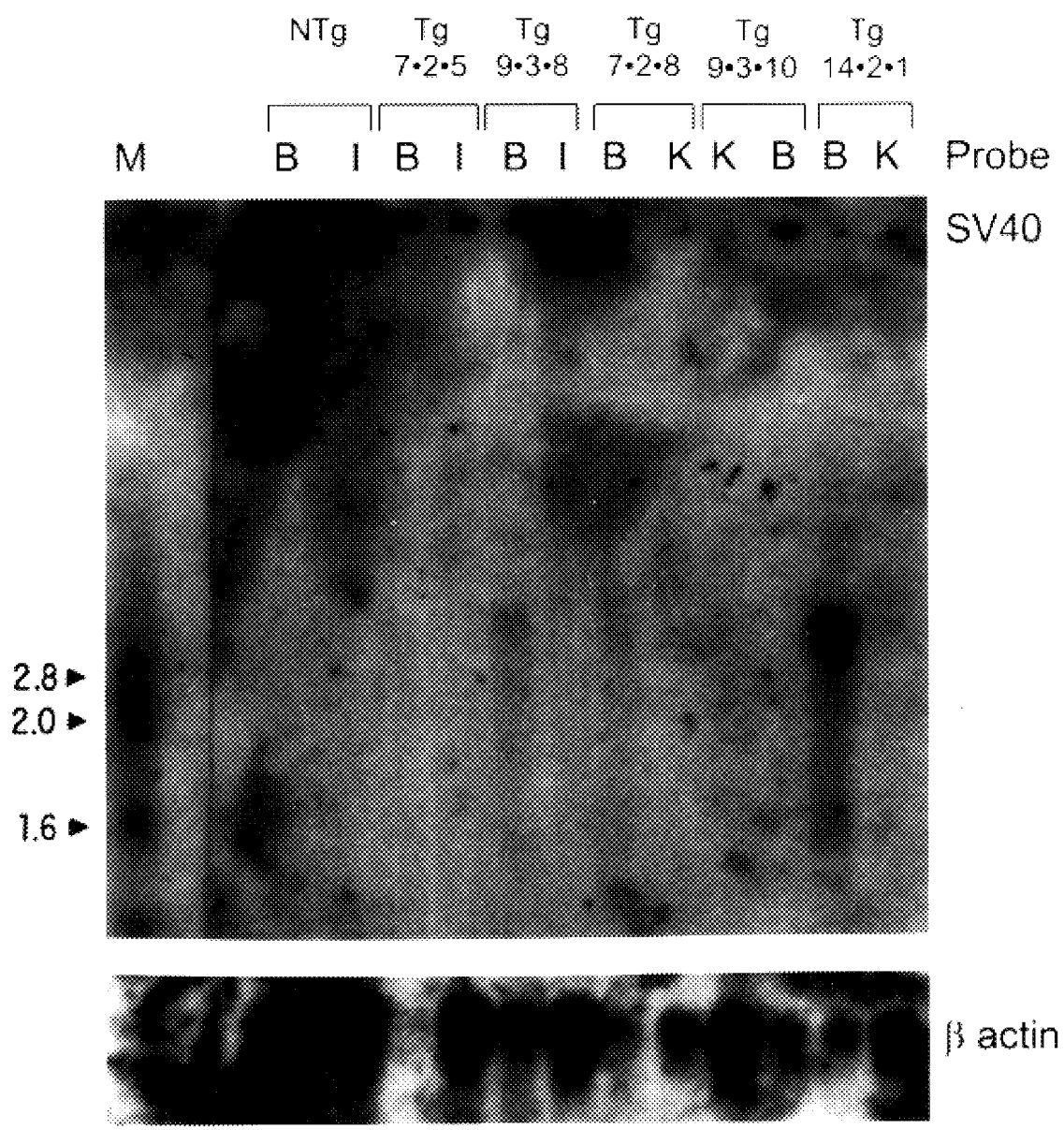
FIG. 2. RNA analysis of APP 751 FAD founders. Upper panel: Northern blot analysis of APP 751 FAD transgenic (Tg) and age-matched, non-transgenic (NTg) F1 mice. Samples (about 4 µg) of poly A$^+$ mRNA from brain (B), kidney (K) and intestine (I) were resolved on a MOPS formaldehyde gel and transferred to a nylon membrane. The RNA was hybridized with $^{32}$p labeled transgene specific SV40 sequences. Predominant brain-specific expression was seen in line 14.2 F1 transgenic animals. Line 7.2 and Line 9.3 transgenic animals exhibited a lower level of expression. Bottom panel: The Northern blot was hybridized with a $^{32}$p labeled β-actin probe and the relative amount of poly A$^+$ mRNA loaded in the different lanes was estimated.

Total RNA was isolated from mouse tissues including brain, liver, lung, kidney, spleen, intestine, heart, thymus, and skeletal muscle by the method of Chomczynski and Sacchi (*Anal. Biochem.* (1987) 162, 156–159). Poly A$^+$ mRNA was purified from total RNA using mini-oligo (dT) cellulose spin column kit with methods as outlined by the suppliers (5 Prime>3 Prime Inc.®). Approximately 4 μg of poly (A)$^+$ mRNA was resolved on a MOPS-formaldehyde gel at 5 Volts/cm for 3–4 hours at room temperature with constant recirculation of the buffer. At the end of the run, RNA was visualized by ethidium bromide staining. Following staining, the gel was repeatedly rinsed in DEPC treated water to remove excess formaldehyde. To assure efficient transfer of the RNA, the gel was soaked in 50 mM NaOH and 10 mM NaCl for 20 minutes and neutralized in 100 mM Tris-HCl (pH 7.5) for 30 minutes. Finally, the RNA was transferred to a nylon membrane in 20×SSC. To identify the APP 751 FAD transgenic transcripts, the filter was hybridized with transgene-specific SV40 sequences. At least a 10-fold increase in the APP 751 RNA expression levels in the brain of the 14.2 transgenic line was observed in comparison to the other transgenic samples, while control brain samples never showed expression of the transgenes (FIG. 2). In addition, APP transgene expression could not be detected in other tissues from the transgenic animals suggesting neuronal-specific expression of the hThy-1 promoter. The ability to detect the APP 751 cDNA in Northern blot analysis indicates that the RNA is abundantly expressed in the central nervous system. Previous reports relied on reverse transcriptase PCR technology, presumably due to the low level of expression of the transgene.

C. RT-PCR

Figure 3A:
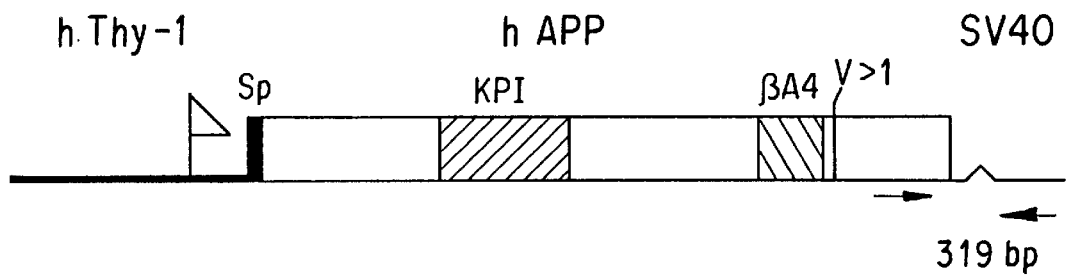
FIGS. 3(A–B). RT-PCR analysis of APP751 FAD. One microgram of total RNA from various tissues of a perfused transgenic animal (line 14.2) was reverse transcribed and subsequently amplified using AmpliTaq DNA polymerase. The amplified products were resolved on a 0.8% agarose gel, blotted to a nylon membrane, and hybridized with SV40 sequences. Predominantly APP 751 mRNA expression was found in brain and while expression was negligible in most other tissues.
Figure 3B:
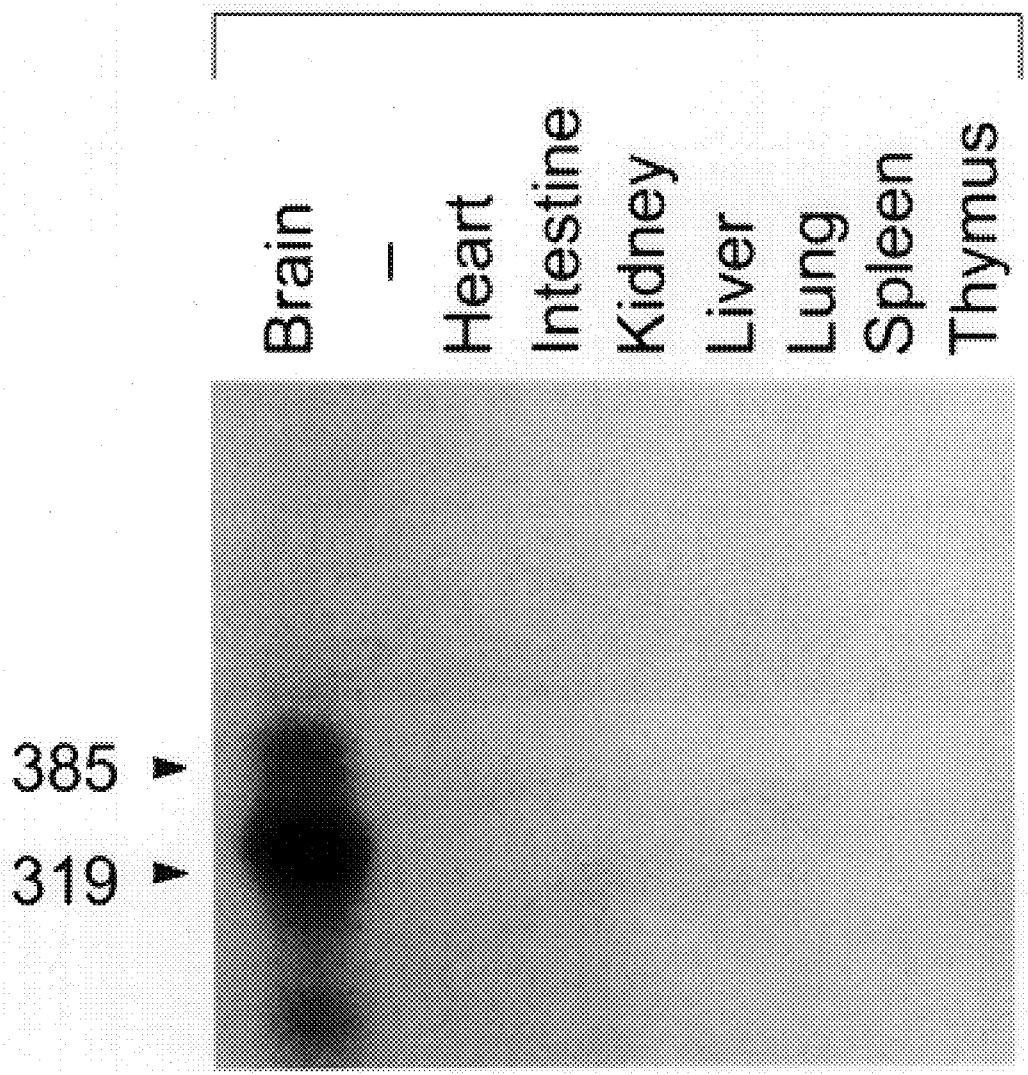
Figure 4A:
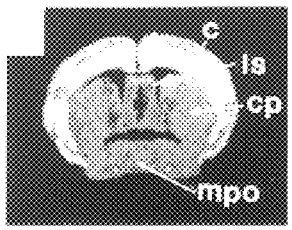
FIGS. 4(A–L). Localization of APP 751 FAD RNA by in situ hybridization. Computer-generated pseudo-color images of representative in situ hybridization X-ray film autoradiograms show expression of human APP 751 FAD mRNA in various brain areas of the transgenic mice. The 14.2 line (rostral to caudal; labeled A, B, C); the 9.3 line (E, F, G); and the 7.2 line (I, J, K). The highest level of mRNA expression was found in the brains of mice belonging to the 14.2 line with expression throughout the brain, but was particularly dense in the cortex (C) and hippocampus (h). High mRNA levels were also found in the amygdala (am), the superficial layers of the superior colliculus (sc) and the central grey (cg). Lower levels of expression were found in other areas, e.g., in the hypothalamus-medial preoptic area (mpo) and arcuate nucleus (arc), the lateral septum (ls) and caudate putamen (cp). When brain sections were taken from the 14.2 line (D), the 9.3 line (H) and the 7.2 line (L) and hybridized with $^{35}$S labeled control 'sense' probe (complementary to the 'antisense' probe), mRNA signals could not be obtained, showing the specificity of the RNA signals obtained with the labeled antisense human APP 751FAD mRNA probe.
Figure 4E:
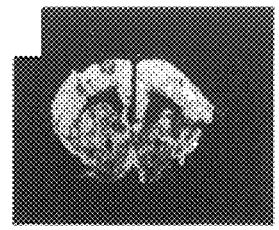
Figure 4I:
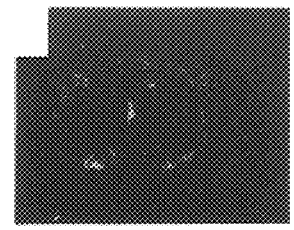
Figure 4B:
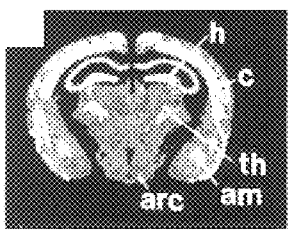
Figure 4F:
Figure 4J:
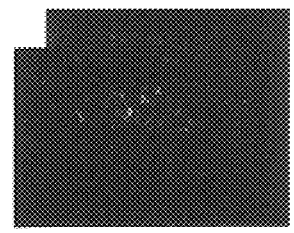
Figure 4C:
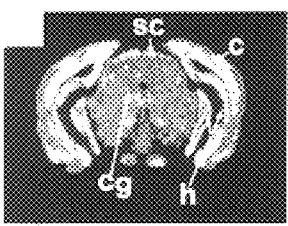
Figure 4G:
Figure 4K:
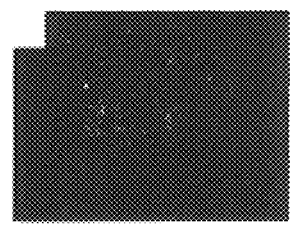
Figure 4D:
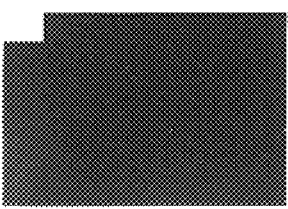
Figure 4H:
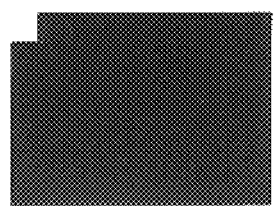
Figure 4L:
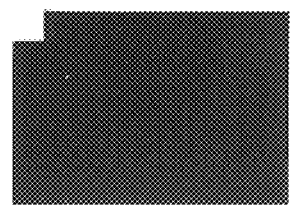

A reverse transcription polymerase chain reaction (RT-PCR) assay for rapidly analyzing the transgenic mRNA in the APP transgenic animals was also used analyzing total RNA isolated from different tissues for FAD APP 751 expression. To avoid contamination of the tissue with blood, total RNA for RT-PCR analysis was prepared from saline perfused transgenic animals. At least 1 μg of total RNA was reverse transcribed at 42° C. in the presence of human placental RNase inhibitor. PCR amplification was performed in the presence of the 519-5 (CGGGCTCTCCTGATTATTTATCT; SEQ ID NO: 3) and 519-3 primers (AAAGGCATTCCACCA CTGCT; SEQ ID NO: 4) and components of GeneAmp®RNA PCR Kit (Perkin Elmer Cetus Instruments) according to the manufacturers instructions. The primers (FIG. 1, arrows below the physical map) were designed across the 66 bp small t intron (FIG. 1; indentation in physical map) to differentiate amplification of the spliced mRNA from intron containing DNA that might contaminate the RNA preparation and to discriminate RNA precursor transcripts from mRNA. The amplification profile included a 2 minute incubation at 95° C. for 1 cycle; 1 minute at 95° C. and 1 minute at 60° C. for 35 cycles and a 7 minute extension cycle at 60° C. Amplifications were carried out in a Bios thermal cycler. The PCR products were resolved on a 1.5% agarose gel in a Tris Acetate-EDTA buffer and transferred to a nylon membrane and hybridized with SV40 sequences (FIG. 3). An expected RNA derived 319 bp fragment was generated in brain samples from the F2 progeny of all three independently generated transgenic lines (7.2, 9.3 and 14.2; only line 14.2 results are shown in FIG. 3). Amplification signals could not be observed with RNA from a non-transgenic control brain sample.

D. In situ Hybridization

The animals were euthanized, the brains quickly removed under aseptic conditions and immediately frozen in isopentane on dry ice at –35° C. and stored at –70° C. Coronal or sagittal sections~10 μm) were then cut in a cryostat (Reichert) at –18° C. to –20° C. Sections were thaw mounted on "Probe On" slides (Fisher Scientific), air-dried thoroughly (approximately 1 h), fixed in 4% paraformaldehyde in 0.1 M phosphate buffered saline (PBS; pH7.4) for 5 min., rinsed in PBS for 2 min., delipidated and dehydrated in an ethanol series (50, 70 and 95%) (5 min. each and stored in 95% ethanol at +4° C.).

The 'antisense' oligonucleotide probe specific for the human APP 751 mRNA was 40 bases long and was complementary to bases 1138–1177 of the human APP gene (5'-ACT GGC TGC TGT TGT AGG AAT GGC GCT GCC ACA CAC GGC C -3'; SEQ ID NO: 5) (Ponte et al., (1988), *Nature*, 331, 525–527). It was synthesized on an Applied Biosystems DNA synthesizers (Model 394) and purified on a 8% polyacrylamide/8M urea preparative sequencing gel. When used in in situ hybridization experiments, this probe gave hybridization signal for APP 751 in human and monkey brain sections, but not in mouse brain sections, indicating its specificity for human APP 751 (no cross hybridization with mouse APP 751).

The APP 751 probe was 3'-end labeled with [$^{35}$S] deoxyadenosine 5'-(α-thiotriphosphate) ([$^{35}$S]dATP) (1415 Ci/mMol) (New England Nuclear) in a 30:1 molar ratio of [$^{35}$S]dATP:oligonucleotide using terminal deoxynucleotidyl transferase (25 units; Boehringer Manheim) for 15 min. at 37° C. in reaction buffer containing 1 M potassium cacodylate, 125 mM Tris-HCl, 1.25 mg/ml bovine serum albumin (pH 6.6) and 25 mM cobalt chloride. Radiolabeled oligonucleotide was separated from unincorporated nucleotides using Sephadex G50 spin columns; 2 μl of 1 M dithiothreitol (DTT) was added to the eluate to prevent cross linking of sulfur residues. The specific activities of the labeled APP 751 oligonucleotide probe in several labeling reactions varied from 1.2–2.3×10$^9$ cpm/μg.

Hybridizations of mouse brain sections were carried out essentially as previously described (Sirinathsinghji et al., (1990), *Neuroscience*, 34, 675–686; Sirinathsinghji and Dunnett (1993), In Molecular imaging in neuroscience (Ed. Sharif, NA), 43–70). Briefly, sections were removed from the alcohol, air-dried for about 1 h and incubated with 0.4–1.0×10$^6$ cpm of 35S labeled probe in 100 ml hybridization buffer containing 50% deionized formamide, 4× saline sodium citrate (SSC), 5× Denhardt's, 200 μg/ml acid-alkali denatured salmon sperm DNA, 100 μg/ml long chain polyadenylic acid, 25 mM Sodium phosphate pH7.0, 0.1 mM sodium pyrophosphate, 10% dextransulphate, and 40 mM DTT.

To define non-specific hybridization, adjacent slide mounted sections were incubated with labeled oligonucleotide probe in the presence of an excess (×00) concentration of unlabeled oligonucleotide probe or with a sense probe from the same region. Parafilm coverslips were gently placed over the sections which were then put in humidified containers and incubated overnight (about 16 h) at 37° C. Following hybridization, the sections were washed for 1 h in 1×SSC at 57° C. and then rinsed briefly in 0.1×SSC, 70% and 95% ethanol, air-dried and then exposed to Amersham Hyperfilm, β-max X-ray film for 2–17 days.

In situ hybridization was performed on sections from 3 animals from the 14.2 founder (14.2.5.13, 14.2.3.25 and 14.2.3.57) and two control non-transgenic litter mates (14 2.5.12 and 14.2.3.26) and animals from transgenic lines 7.2 and 9.3 and their non-transgenic littermates. Autoradiograms (2-day-exposure) of hybridized sections from all three transgenic animals showed dense homogeneous APP751 mRNA expression throughout the brain. Expression was particularly abundant in all cortical areas (prefrontal, cingulate, frontal, occipital, piriform) hippocampus (dentate gyrus, CA3, CA2, CA1 fields and amygdala). Dense but comparatively less expression was found in the septum, caudate-putamen and thalamus (FIG. 4). The specificity of the mRNA signal was confirmed by results showing that (1) adjacent sections from the three transgenic animals hybridized with labeled oligonucleotide in the presence of 100-fold excess of unlabeled oligonucleotide gave no hybridization signal and (2) sections from control non-transgenic animals (14.2.3.26 and 14.2.5.12) hybridized with labeled oligonucleotide probe gave no hybridization signal in any brain areas and (3) hybridization with the sense probe gave no detectable signal (FIG. 4).

E. APP Protein Detection by Western Blotting

Figure 5:
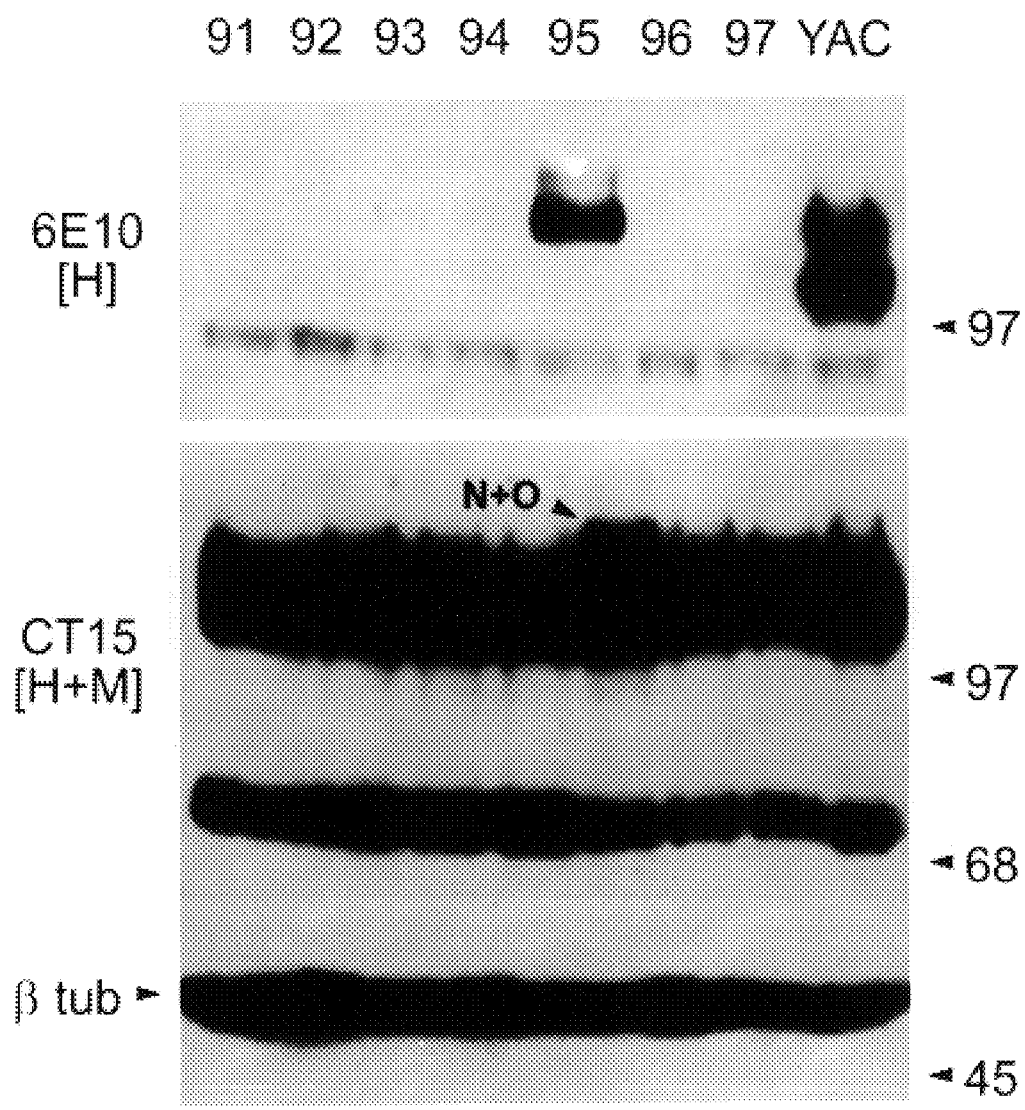
FIG. 5. APP 751 (V-I) protein analysis by Western blotting. Western blotting of brain protein lysates from different transgenic animals (91–95) and non-transgenic control animals (96, 97) with a human-specific antibody (Ab) 6E10 (Kim et al., (1990) Neurosci. Res. Commun. 7, 113–122; Kim et al., (1988) Neurosci Res. Commun. 2, 121–130). The top panel shows reactivity with the 6E10 Ab; the middle panel shows reactivity with CT15 Ab; recognizing human and mouse APP; and the bottom panel shows reactivity with a β-tubulin control Ab. Animal 95 (line 14.2 transgenics) expresses a large quantity of APP 751 protein at levels comparable to the 500 kb YAC derived human APP protein expressed in mice (labeled YAC; Lamb et al., (1993) *Nature Genetics* 5, 22–30). N+O in the CT15 panel represents the fully modified, glycosylated 751 protein in the line 95 animals. Line 9.3 and 7.2 animals (91, 92 and 93, 94, respectively) had lower levels of APP protein.

The human APP 751 protein was also identified by Western blotting in lysates from brains from these transgenic mice (FIG. 5). The quantity of protein APP 751 protein identified equaled that of the endogenous mouse APP 751 protein (see Figure legend for details).

E. Immunocytochemistry

Figure 6A:
FIGS. 6(A–B). APP751 FAD expression in mouse brain. Brains from transgenic mice that overexpress the human APP gene were analyzed. Using a monoclonal antibody to the N-terminal end of human APP (Clone 22C11, Boehringer Mannheim; dilution 1:20), intensely immunoreactive neurons were found in the cortex and hippocampus in the brains of APP751 FAD transgenic 14.2 founder (18 months old). Non-transgenic control (15 month old) did not show this staining pattern. The intensity of the staining appeared to be age-related. This accumulation of APP immunoreactivity in neurons of the transgenic mice appeared to be granular and deposit-like in appearance.
Figure 6B:
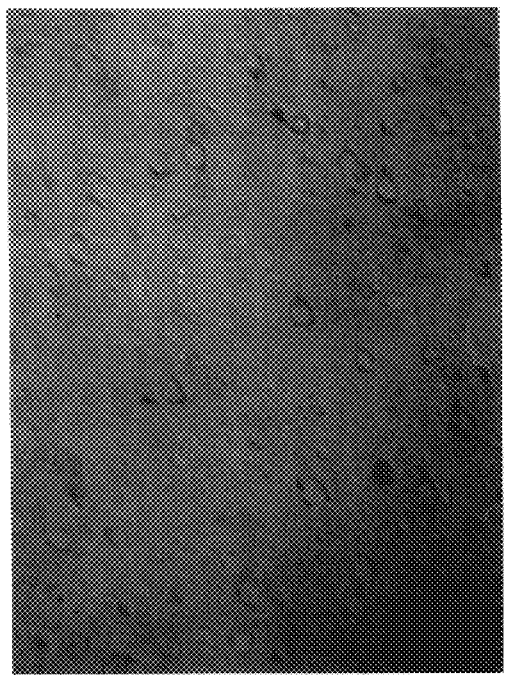

Mice were deeply anaesthetized and then transcardially perfused with saline, followed by 4% paraformaldehyde in 0.1 M phosphate buffered saline (PBS). Brains were removed and post-fixed in 4% paraformaldehyde for 1 h, then placed in 30% sucrose in 0.1 M PBS at 4° C. until the brains sank and then frozen in isopentane at −35° C. and stored at −70° C. until sections were cut. Sections (20 mM) were cut in a cryostat (Reichert) and stored in anti-freeze at −20° C. Sections were removed from anti-freeze and washed through 5 changes of PBS and Triton X100 (0.3%). Background staining was blocked by incubating sections in normal goat serum (3% in PBS and Triton) for 90 minutes. The sections were then incubated overnight at 4° C. with a rabbit polyclonal antibody to synthetic β-amyloid (1–40) peptide (Boehringer Manheim). Again, the sections were washed thoroughly in PBS and Triton (3×5 minutes) and then immunostained using a standard avidin-biotin complex method (Vector Laboratories, Peterborough, UK). Stained sections were mounted on gelatin subbed air-dried and mounted in Depex. Commercially available monoclonal antibodies to the N-terminal end of the B-APP (clone 22C11, Boehringer Mannheim) intensely stained neurons in the cortex and hippocampus (CA3-CA1) of the APP 751 FAD mice that were 18 months old. This staining pattern was not homogeneous and appeared granular in neurons and neurites. This deposit-like accumulation of intraneuronal βAPP immunoreactivity was not seen in the control non-transgenic mice (FIG. 6).

EXAMPLE 4

Cell Culture

The transgenic animals of the invention may be used as a source of cells for cell culture. Brain tissues of transgenic mice are analyzed for the presence of human amyloid precursor protein by directly analyzing DNA or RNA or by assaying brain tissue for the protein expressed by the gene. Cells of brain tissues carrying the gene may be cultured using standard culture techniques that are well-known in the art.

EXAMPLE 5

Screening Assays

The transgenic animals and cells derived from the transgenic animals may be used to screen for compounds that modulate expression of human amyloid precursor protein. Modulation may occur at a variety of levels including but not limited to DNA or RNA or protein or combinations thereof.

One method of determining the ability of a compound to modulate the expression of human amyloid precursor protein in a transgenic non-human animal having cells containing a gene encoding a familial form of the human amyloid precursor protein APP 751 comprises: (a) treating the transgenic animal with the compound; (b) measuring the expression or aggregation of human amyloid precursor protein in the treated animal; and (c) comparing the measurement of step (b) with a control.

A method of determining the ability of a compound to modulate the expression of human amyloid precursor protein in cells derived from a transgenic animal comprises: (a) treating the cells with the compound; (b) measuring the expression or aggregation of human amyloid precursor protein in the treated cells; and (c) comparing the measurement of step (b) with a control.

EXAMPLE 6

Nucleotide Sequence of Relevant FAD APP 751 β-A4 Sequence

The 43 amino acid β-A4 domain is highlighted in bold. The V-I substitution is boxed (FIG. 7).

What is claimed is:

1. A transgenic mouse whose genome comprises and expresses a nucleic acid construct comprising a Thy-1 promoter operably linked to a DNA sequence encoding a human FAD APP consisting of a valine to isoleucine amino acid substitution at position 717, wherein said expression results in amyloid plaques appearing in the brain of the mice at about 18 months of age.

2. A method of determining the ability of a compound to modulate human amyloid precursor protein activity comprising:

(a) administering a compound to a transgenic mouse whose genome comprises and expresses a nucleic acid construct comprising a Thy-1 promoter operably linked to a DNA sequence encoding a human FAD APP consisting of a valine to isoleucine amino acid substitution at position 717, wherein said expression results in amyloid plaques appearing in the brain of the mice at about 18 months of age;

(b) measuring the expression or aggregation said human amyloid precursor protein in the brain of the treated mouse;

(c) providing a control mouse, wherein the control mouse is a transgenic mouse whose genome comprises and expresses a nucleic acid construct comprising a Thy-1 promoter operably linked to a DNA sequence encoding a human FAD APP consisting of a valine to isoleucine amino acid substitution at position 717, wherein said expression results in amyloid plaques appearing in the brain of the mice at about 18 months of age;

(d) measuring the expression or aggregation of said human amyloid precursor protein in the brain of the control mouse; and (e) comparing the measurement of step (b) with the measurement of step (c), where the ability of the compound to modulate said human amyloid precursor protein activity is evidenced by an alteration in the expression or aggregation of human amyloid precursor protein between the brains of said mice.

3. The method according to claim 2, wherein measuring the expression or aggregation of said human amyloid precursor protein is measuring a cleavage product of said amyloid precursor protein.

4. A cell line isolated from the mouse of claim 1, wherein said cell expresses human FAD APP consisting of an amino acid substitution at position 717.

5. A method of determining the ability of a compound to modulate human amyloid precursor protein activity comprising:

(a) administering a compound to neuronal cells isolated from a transgenic mouse whose genome comprises and expresses a nucleic acid construct comprising a Thy-1 promoter operably linked to a DNA sequence encoding an FAD APP consisting of a valine to isoleucine amino acid substitution at position 717, wherein said cell expresses FAD APP consisting of an amino acid substitution at position 717;

(b) measuring the expression or aggregation said human amyloid precursor protein in the treated neuronal cells;

(c) providing control neuronal cells isolated from a transgenic mouse whose genome comprises and expresses a nucleic acid construct comprising a Thy-1 promoter operably linked to a DNA sequence encoding a human FAD APP consisting of a valine to isoleucine amino acid substitution at position 717, wherein said cell expresses FAD APP consisting of an amino acid substitution at position 717;

(d) measuring the expression or aggregation of said human amyloid precursor protein in the control neuronal cells; and (e) comparing the measurement of step (b) with the measurement of step (c), where the ability of the compound to modulate said human amyloid precursor protein activity is evidenced by an alteration between the expression or aggregation of human amyloid precursor protein in said neuronal cells.

6. The method according to claim 5, wherein measuring the expression or aggregation of said human amyloid precursor protein is measuring a cleavage product of said amyloid precursor protein.

* * * * *

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
        (A) LENGTH: 20 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO:1:

TAATACGACT CACTATAGGG                                                   20

(2) INFORMATION FOR SEQ ID NO:2:

(i) SEQUENCE CHARACTERISTICS:
        (A) LENGTH: 94 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO:2:

ACGTCGACTC TAGAAGATCT TCGACTCGAG ATCGATGGTA CCCGGGCAGG TTCAAGCTTC        60

TGGGATCTCA GTCCATGGTT CTGGGATCTC AGTC                                   94

(2) INFORMATION FOR SEQ ID NO:3:

(i) SEQUENCE CHARACTERISTICS:
        (A) LENGTH: 23 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO:3:

CGGGCTCTCC TGATTATTTA TCT                                               23

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO:4:

AAAGGCATTC CACCACTGCT                                                   20

(2) INFORMATION FOR SEQ ID NO:5:

(i) SEQUENCE CHARACTERISTICS:
        (A) LENGTH: 40 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO:5:

ACTGGCTGCT GTTGTAGGAA TGGCGCTGCC ACACACGGCC                         40